United States Patent
Otsuki et al.

(10) Patent No.: US 11,507,689 B2
(45) Date of Patent: Nov. 22, 2022

(54) MEDICAL DATA COMMUNICATION APPARATUS, SERVER, MEDICAL DATA COMMUNICATION METHOD AND MEDICAL DATA COMMUNICATION PROGRAM

(71) Applicant: TOYOTA JIDOSHA KABUSHIKI KAISHA, Toyota (JP)

(72) Inventors: Nobuhisa Otsuki, Toyota (JP); Takuya Iwata, Toyota (JP); Masayoshi Tsuchinaga, Nisshin (JP); Hodaka Kito, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 16/156,064

(22) Filed: Oct. 10, 2018

(65) Prior Publication Data
US 2019/0163930 A1 May 30, 2019

(30) Foreign Application Priority Data
Nov. 24, 2017 (JP) .............................. JP2017-226003

(51) Int. Cl.
*G06F 21/62* (2013.01)
*G16H 10/60* (2018.01)
*G16H 20/30* (2018.01)

(52) U.S. Cl.
CPC ......... *G06F 21/6245* (2013.01); *G16H 10/60* (2018.01); *G06F 21/6263* (2013.01); *G16H 20/30* (2018.01); *H04L 2209/04* (2013.01)

(58) Field of Classification Search
CPC . G06F 21/6245; G06F 21/6263; G16H 10/60; G16H 20/30; H04L 2209/04
See application file for complete search history.

(56) References Cited

U.S. PATENT DOCUMENTS 9,021,161 B2 * 4/2015 Vlach ................ A61B 5/303
710/63
9,129,283 B1 * 9/2015 Raju .................. G06Q 20/3829
(Continued)

FOREIGN PATENT DOCUMENTS

CN 106341244 A * 7/2015
JP 2012208737 A * 10/2012
(Continued)

OTHER PUBLICATIONS

John Spacey, Pull vs Push Technology, Mar. 5, 2017 (Year: 2017).*
(Continued)

*Primary Examiner* — John A Follansbee
*Assistant Examiner* — Fadi Haj Said
(74) *Attorney, Agent, or Firm* — Oblon, McClelland, Maier & Neustadt, L.L.P.

(57) ABSTRACT

A medical data communication apparatus includes a data acquisition unit configured to acquire medical data of a subject output from a medical device from the medical device, the medical device being connected for communication with the medical data communication apparatus without an external network intervening therebetween; a modification unit configured to modify the medical data based on a modification instruction received from a server, the server being connected for communication with the medical data communication apparatus through an external network, the modification instruction being for modifying specific information in the medical data; and an output unit configured to output the medical data modified by the modification unit to the external network based on a request from the server.

9 Claims, 8 Drawing Sheets

(BEFORE MODIFICATION)

(AFTER MODIFICATION)

(56) References Cited

U.S. PATENT DOCUMENTS

| | | | | |
|---|---|---|---|---|
| 9,411,610 | B2* | 8/2016 | Urakawa | G06F 9/452 |
| 9,883,543 | B2* | 1/2018 | Maheshwari | H04W 4/08 |
| 9,999,013 | B2* | 6/2018 | Cacioppo | G09B 7/02 |
| 10,286,148 | B2* | 5/2019 | Case | A61M 5/1723 |
| 2004/0069311 | A1* | 4/2004 | Sasaki | G06F 19/321 |
| | | | | 128/897 |
| 2006/0094442 | A1* | 5/2006 | Kirkup | H04W 88/02 |
| | | | | 455/455 |
| 2006/0282884 | A1* | 12/2006 | Pomerantz | H04L 63/0428 |
| | | | | 726/5 |
| 2007/0179815 | A1* | 8/2007 | Vining | G06F 19/3418 |
| | | | | 705/3 |
| 2009/0125329 | A1 | 5/2009 | Kue | |
| 2009/0177249 | A1* | 7/2009 | Roberts | G16H 40/40 |
| | | | | 607/60 |
| 2009/0254664 | A1* | 10/2009 | Wada | H04L 67/14 |
| | | | | 709/227 |
| 2011/0021317 | A1 | 1/2011 | Lanfermann | |
| 2011/0167133 | A1* | 7/2011 | Jain | H04L 67/12 |
| | | | | 709/219 |
| 2012/0057595 | A1 | 3/2012 | Awano | |
| 2012/0182939 | A1* | 7/2012 | Rajan | A61B 5/0008 |
| | | | | 370/328 |
| 2013/0208966 | A1* | 8/2013 | Zhao | G06F 9/5072 |
| | | | | 382/131 |
| 2013/0339317 | A1* | 12/2013 | Kim | G06F 16/1748 |
| | | | | 707/692 |
| 2014/0059118 | A1* | 2/2014 | Pidady | H04L 67/06 |
| | | | | 709/203 |
| 2014/0142984 | A1* | 5/2014 | Wright | G06F 19/321 |
| | | | | 705/3 |
| 2016/0203264 | A1* | 7/2016 | Danner | H04N 1/4493 |
| | | | | 382/128 |
| 2018/0220872 | A1 | 8/2018 | Tashiro | |
| 2018/0241758 | A1* | 8/2018 | Inoue | G06F 21/60 |
| 2018/0342314 | A1* | 11/2018 | Tichy | G16H 30/20 |

FOREIGN PATENT DOCUMENTS

| | | |
|---|---|---|
| JP | 2015-7885 | 1/2015 |
| JP | 2015-125514 A | 7/2015 |
| JP | 2015-186531 A | 10/2015 |
| JP | 2016-105251 A | 6/2016 |
| JP | 6187208 | 8/2017 |
| WO | 2017-068905 A1 | 4/2017 |

OTHER PUBLICATIONS

Suzuki, H. et al., "Anonymization server system for DICOM images", Proceedings of SPIE, XP055143286, vol. 6516, Mar. 8, 2007, pp. 65160Z-1-65160Z-9.

Padilla-Lõpez, J. R. et al., "Visual Privacy by Context: A Level-Based Visualisation Scheme", Image Analysis and Recognition: 11$^{th}$ International Conference, XP055496733, vol. 8867, Jan. 1, 2014, pp. 333-336.

* cited by examiner

TRAINEE ID 01234567  NAME ICHIRO SUZUKI MALE   TRAINING DATA

DATE OF BIRTH 1960/04/02
AGE            32 YEARS OLD

NUMBER OF TRAINING
TRIALS (TIMES)               6
AVERAGE EVALUATION (1-5)   3.5
BODY TEMPERATURE CHANGE (°C) 36.2 → 36.8
PULSES CHANGE (TIMES)    90 → 118

COMMENT FROM PHYSICAL THERAPIST

IT APPEARS THAT MR. SUZUKI DRAGS
HIS FOOT. IF HIS ANXIETY FOR
WALKING IS LESSENED,
HIS SYMPTOM WILL IMPROVE.

MOVING LEG IMAGE

A000325.mp4    B000325.mp4

MANAGED AND
CREATED BY  SAKURAGAOKA HOSPITAL

| NUMBER OF TRIALS | 1 |
|---|---|
| SWINGING ASSISTING LEVEL | 2 |
| KNEE EXTENDING ASSISTING LEVEL | 1 |
| TREADMILL SPEED | 2.5 |
| TRAINING EVALUATION | 5 |
| FAILURE RATE (%) | 14 |
| EVALUATION FOR EACH WALKING | |
| 1 | ○ |
| 2 | × |
| 3 | ○ |
| 4 | ○ |
| 5 | ○ |
| 6 | ○ |
| 7 | ○ |

| NUMBER OF TRIALS | 2 |
|---|---|
| SWINGING ASSISTING LEVEL | 1 |
| KNEE EXTENDING ASSISTING LEVEL | 1 |
| TREADMILL SPEED | 2.5 |
| TRAINING EVALUATION | 4 |
| FAILURE RATE (%) | 20 |
| EVALUATION FOR EACH WALKING | |
| 1 | ○ |
| 2 | ○ |
| 3 | ○ |
| 4 | × |
| 5 | × |
| 6 | ○ |
| 7 | ○ |
| 8 | ○ |

Fig. 5

| MODIFICATION INSTRUCTION FILE ||
|---|---|
| NAME | UNMODIFIABLE |
| DATE OF BIRTH | UNMODIFIABLE |
| AGE | CLASSIFICATION |
| IDENTIFICATION IMAGE | UNMODIFIABLE |
| MOVING LEG IMAGE | FACE MOSAIC PROCESSING |

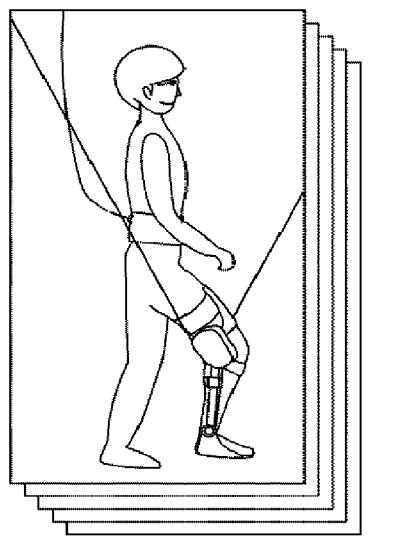
(BEFORE MODIFICATION)
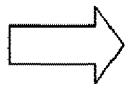
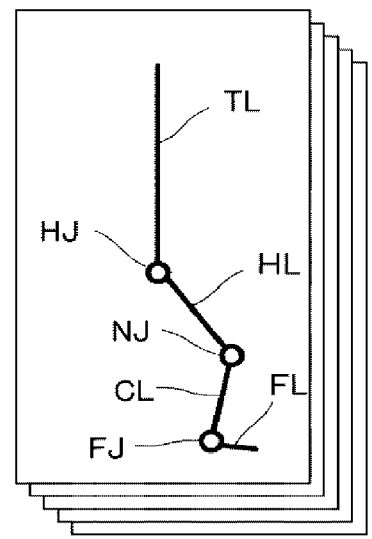
(AFTER MODIFICATION)
Fig. 8

MEDICAL DATA COMMUNICATION APPARATUS, SERVER, MEDICAL DATA COMMUNICATION METHOD AND MEDICAL DATA COMMUNICATION PROGRAM

CROSS REFERENCE TO RELATED APPLICATIONS

This application is based upon and claims the benefit of priority from Japanese patent application No. 2017-226003, filed on Nov. 24, 2017, the disclosure of which is incorporated herein in its entirety by reference.

BACKGROUND

The present disclosure relates to a medical data communication apparatus, a server, a medical data communication method and a medical data communication program.

Medical data of subjects output from medical devices includes a lot of personal information. Therefore, for distributing medical data to an external network such as the Internet, some measures need to be taken so that personal information is not spread even if it is stolen during the distribution. As an example of such measures, a technique for encrypting an entire file including medical data is known. Further, a technique for protecting personal information by replacing specific information with anonymous information is also known. (see Japanese Unexamined Patent Application Publication No. 2015-7885 as an example)

SUMMARY

In the case of using the technique for encrypting data, there is a possibility that personal information may be decrypted and spread. Some predefined information can be replaced with anonymous data as described above. However, the range of personal information that needs to be protected changes according to laws and guidelines regarding medical devices, the needs of the time etc. Especially, since medical devices are often used after they are properly authenticated together with software to be performed, it is practically difficult to frequently update such medical devices as to what kind of information is output to an external network.

In the present disclosure, a technique capable of flexibly changing a range of protection of personal information included in medical data and safely distributing the medical data to an external network will be described.

A first exemplary aspect is a medical data communication apparatus, including: a data acquisition unit configured to acquire medical data of a subject output from a medical device from the medical device, the medical device being connected for communication with the medical data communication apparatus without an external network intervening therebetween; a modification unit configured to modify the medical data based on a modification instruction received from a server, the server being connected for communication with the medical data communication apparatus through the external network, the modification instruction being for modifying specific information in the medical data; and an output unit configured to output the medical data modified by the modification unit to the external network based on a request from the server.

By interposing the medical data communication apparatus between the external network and the medical device as described above, specific information in the medical data can be flexibly modified according to a use environment without changing the medical device, which is needed to be authenticated for a change in its specifications etc. Further, the specific information is modified before being output to the external network. Therefore, there is no possibility that the specific information may be spread before it is modified even when the medical data is stolen in a distribution process on the external network.

In the medical data communication apparatus described above, when the medical data includes image information of the subject, the modification unit may perform a mask processing on at least a part of an image of the image information based on the modification instruction. Further, the image information may be replaced with a CG based on the modification instruction. By performing such image processing, personal information in the image (e.g., an image of text indicating personal information) can also be protected.

Further, in the above-described medical data communication apparatus, when the medical data includes a description section in which information attributed to the subject is described and the attributed information described in the description section is modified based on the modification instruction, the modification unit may make a search as to whether the described attributed information is included in a section other than the description section, and also modify the attributed information found in the search. By performing such additional processing, for example, even when a name of the subject is included in a comment described in a comment section, the name is properly modified so that the attributed information can be thoroughly protected.

A second exemplary aspect is a server connected for communication with a medical data communication apparatus through an external network, the medical data communication apparatus being connected for communication with a medical device without the external network intervening therebetween, the server includes: a transmission unit configured to transmit a modification instruction for modifying specific information in medical data of a subject output from the medical device to the medical data communication apparatus through the external network before the server receives the medical data, and a reception unit configured to receive the medical data modified based on the modification instruction through the external network.

By having the server provide the modification instruction to the medical data communication apparatus interposed between the server and the medical device, instead of providing the modification instruction to the medical device, specific information of medical data can be flexibly modified according to a use environment without changing a medical device needed to be authenticated for a change of a specification, etc. Further, since the server receives the modified medical data, there is no possibility that the specific information may be spread before it is modified even when the medical data is stolen in a distribution process on the external network.

A third exemplary aspect is a medical data communication method including: a data acquisition step of acquiring medical data of a subject output from a medical device from the medical device, the medical device being connected for communication without an intervening external network; a reception step of receiving a modification instruction for modifying specific information in the medical data from a server connected for communication through the external network; a modification step of modifying the medical data based on the specific information; and an output step of outputting the medical data modified by the modification step to the external network based on a request from the server.

Further, a fourth exemplary aspect is a method for medical data communication between a medical data communication device and a server, the medical data communication device being connected for communication with a medical device without an external network intervening therebetween, the server being connected for communication with the medical data communication apparatus through the external network, the method including: a transmission step of transmitting a modification instruction for modifying specific information in medical data of a subject output from the medical device to the medical data communication apparatus through the external network before receiving the medical data, and a reception step of receiving the medical data modified based on the modification instruction through the external network.

According to the medical data communication methods in accordance with the third and fourth exemplary aspects described above, specific information of medical data can be flexibly modified according to a use environment without changing the medical device, which is needed to be authenticated for a change in its specifications etc. Further, the specific information is modified before being output to the external network. Therefore, there is no possibility that the specific information may be spread before it is modified even when the medical data is stolen in a distribution process on the external network.

A fifth exemplary aspect is a medical data communication program for causing a computer in a medical data communication device to perform: a data acquisition step of acquiring medical data of a subject output from a medical device from the medical device, the medical device being connected for communication without an intervening external network; a reception step of receiving a modification instruction for modifying specific information in the medical data from a server connected for communication through the external network; a modification step of modifying the medical data based on the specific information; and an output step of outputting the medical data modified by the modification stop to the external network based on a request from the server.

Further, a sixth exemplary aspect is a program for medical data communication between a medical data communication device and a server, the medical data communication device being connected for communication with a medical device without an external network intervening therebetween, the server being connected for communication with the medical data communication apparatus through the external network, the program being adapted for causing a computer in a server to perform: a transmission step of transmitting a modification instruction for modifying specific information in medical data of a subject output from the medical device to the medical data communication apparatus through the external network before receiving the medical data, and a reception step of receiving the medical data modified based on the modification instruction through the external network.

According to the medical data communication methods in accordance with the fifth and sixth exemplary aspects described above, specific information of medical data can be flexibly modified according to a use environment without changing the medical device, which is needed to be authenticated for a change in its specifications etc. Further, the specific information is modified before being output to the external network. Therefore, there is no possibility that the specific information may be spread before it is modified even when the medical data is stolen in a distribution process on the external network.

The above and other objects, features and advantages of the present disclosure will become more fully understood from the detailed description given hereinbelow and the accompanying drawings which are given by way of illustration only, and thus are not to be considered as limiting the present disclosure.

BRIEF DESCRIPTION OF DRAWINGS

FIG. 5 shows a state in which an example of training data is visibly displayed before it is modified;

FIG. 6 shows contents of a modification instruction file;

FIG. 7 shows a state in which an example of training data is visibly displayed after it is modified;

FIG. 8 shows other examples of modifying images; and

DESCRIPTION OF EMBODIMENTS

Hereinafter, although the present disclosure will be described with reference to embodiments of the invention, the present disclosure according to claims is not limited to the following embodiments. Further, all the components described in the following embodiments are not necessarily indispensable for means to solve problems.

Figure 1:
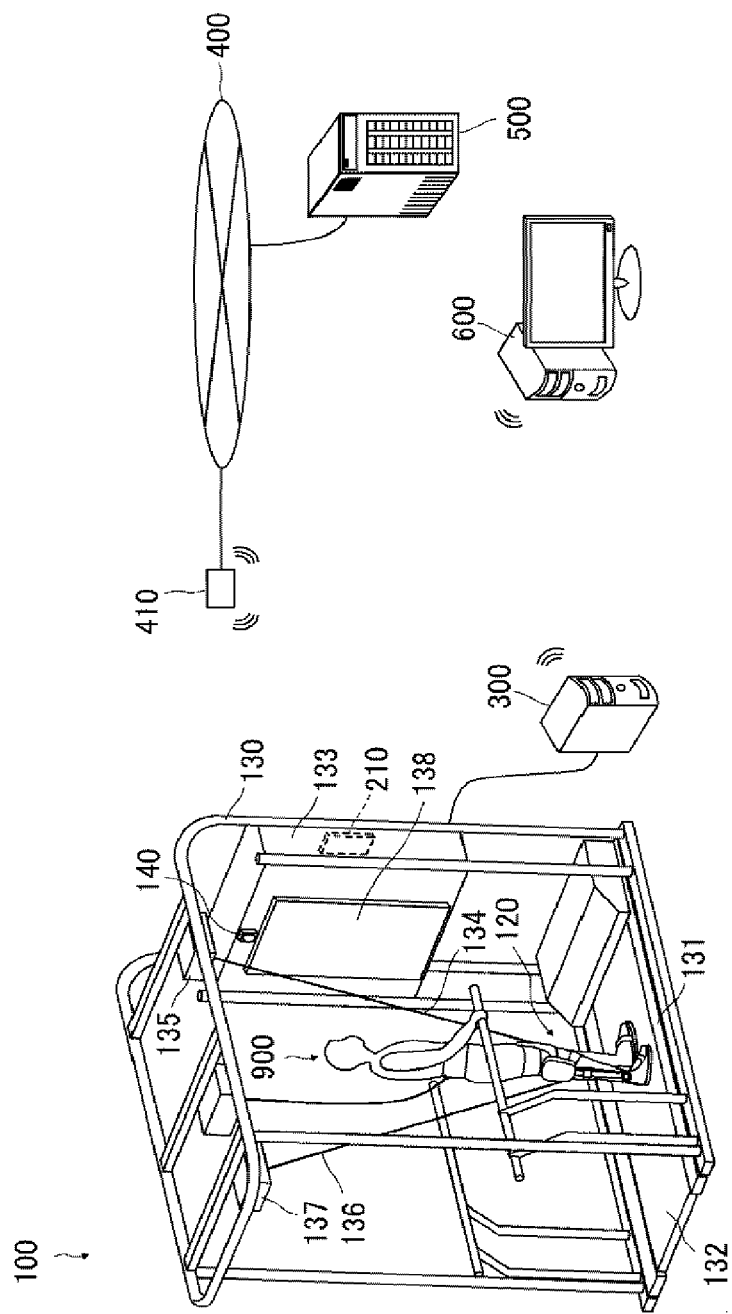
FIG. 1 is an overall conceptual diagram of a walking training system according to this embodiment.

FIG. 1 is an overall conceptual diagram showing a walking training system according to this embodiment. The walking training system mainly includes a walking training apparatus 100, an external communication apparatus 300 and a server 500. The walking training apparatus 100 is an apparatus by which a trainee 900, who is, for example, a hemiplegia patient suffering from paralysis in one of his/her legs, does walking training. The walking training apparatus 100 is an example of medical devices and outputs training data generated by associating a training result of the trainee 900 with information attributed to the trainee 900, such as the name of the trainee 900. The trainee 900 is a subject and the training data of the trainee 900 is handled as medical data showing a status of rehabilitation of the subject.

The walking training apparatus 100 mainly includes a control panel 133 attached to a frame 130 forming an overall framework, a treadmill 131 on which the trainee 900 walks, and a walking assistance apparatus 120 attached to the diseased leg, i.e., the leg on the paralyzed side of the trainee 900. The frame 130 is disposed on the treadmill 131 mounted on a floor surface in a standing state. The treadmill 131 rotates a ring-shaped belt 132 by using a motor (not shown). The treadmill 131 is an apparatus which urges the trainee 900 to walk. The trainee 900, who is performing walking training, gets on the belt 132 and tries to walk according to the movement of the belt 132.

The frame 130 supports the control panel 133 that houses an overall control unit 210 that controls motors or sensors, a training monitor 138 that is formed by, for example, a liquid-crystal panel and shows progress of the training etc. to the trainee 900, and so on. Further, the frame 130 supports a front pulling unit 135 in a position located above and in front of the head of the trainee 900 and a rear pulling unit 137 in a position located above and behind the head of the trainee 900.

A camera 140 functions as an image pickup unit for observing the whole body of the trainee 900. The camera 140 is disposed in the vicinity of the training monitor 138 so that it faces the trainee. The camera 140 includes a set of a lens and an image pickup device having such an angle of view that the whole body of the trainee 900 can be captured. The image pickup device is, for example, a CMOS image sensor, and it converts an optical image formed on an image forming surface into an image signal.

One end of a front wire 134 is connected to a winding mechanism of the front pulling unit 135 and the other end of the front wire 134 is connected to the walking assistance apparatus 120. The winding mechanism of the front pulling unit 135 winds up and pays out the front wire 134 according to the movement of the diseased leg by turning on or off the motor (not shown). Similarly, one end of a rear wire 136 is connected to a winding mechanism of the rear pulling unit 137 and the other end of the rear wire 136 is connected to the walking assistance apparatus 120. The winding mechanism of the rear pulling unit 137 winds up and pays out the rear wire 136 according to the movement of the diseased leg by turning on or off the motor (not shown). By such cooperative operations performed by the front and the rear pulling units 135 and 137, the load (e.g., the weight) of the walking assistance apparatus 120 is cancelled out and hence does not act as a burden on the diseased leg, and a swinging motion of the diseased leg is assisted according to a set level.

For example, an operator who is a training assistant sets an assisting level to a high value for a trainee having severe paralysis. When the assisting level is set high, the front pulling unit 135 winds up the front wire 134 with a relatively strong force in synchronization with the swinging motion of the diseased leg. When the assistance becomes unnecessary as the training proceeds, the operator sets the assisting level to a minimum value. When the assisting level is set to the minimum value, the front pulling unit 135 winds up the front wire 134 with a force by which the weight of the walking assistance apparatus 120 is just cancelled in synchronization with the swinging motion of the diseased leg.

The walking assistance apparatus 120 is attached to the diseased leg of the trainee 900 to assist the trainee 900 in his/her walking. by reducing the burden of extending and bending motions in the knee joint of the diseased leg. Specifically, the burden in the knee joint of the diseased leg is reduced by using the motor (not shown) which generates a driving force to assist the extending and bending motions of the knee joint. Further, the walking assistance apparatus 120 includes a sensor and the like for measuring a load (e.g., a pressure) on the sole, and outputs their outputs as data on the moving leg to the overall control unit 210.

The external communication apparatus 300 is an example of the medical data communication apparatuses. The external communication apparatus 300 has a function of receiving and storing training data output from the walking training apparatus 100. Further, the external communication apparatus 300 has functions of receiving a modification instruction of training data from the server 500 and modifying the training data according to that modification instruction, and a function of transmitting the training data to the server 500. The external communication apparatus 300 is connected to the control panel 133 of the walking training apparatus 100 by, for example, a USB cable, and is also connected for communication to an Internet network 400 as an example of external networks through a wireless communication device 410 which is, for example, a wireless LAN unit.

The server 500 is connected to the Internet network 400 and has a function of accumulating training data received from the external communication apparatus 300. Further, the server 500 has a function of providing accumulated training data according to a request of a terminal 600 connected to the internet network 400. Thus, a data viewer (e.g., a user) can read and view training data accumulated in the server 500 by operating the terminal 600.

Further, the server 500 has functions of generating a modification instruction to modify the specified information of the training data in order to define a data format of the training data distributed through the Internet network 400, and transmitting the modification instruction to the external communication apparatus 300. The details will be described later. Note that training data accumulated by the server 500 is not limited to training data output from one walking training apparatus 100. Further, training data output from a plurality of walking training apparatuses may be comprehensively managed. Further, in this embodiment, the walking training apparatus 100 is given as an example of medical devices. However, the medical data is not limited to training data output from the walking training apparatus 100 and may be data output from various other medical devices or rehabilitation apparatuses. Thus, the server 500 may be an apparatus to comprehensively manage medical data output from each of a plurality of medical devices.

In the above-described walking training system, the walking training apparatus 100 is connected to the Internet network 400 through the external communication apparatus 300 as described above and does not have a communication function of directly connecting to the Internet network 400. That is, the walking training apparatus 100 does not directly output training data to the external network. By interposing the external communication apparatus 300 between the Internet network 400 and the walking training apparatus 100 as described above, it is possible to prevent training data from being leaked from the walking training apparatus 100. The connection between the walking training apparatus 100 and the external communication apparatus 300 is not limited to connection using a USB cable. That is, various communication standards can be adopted as long as they use communication paths that do not go through any external network.

Figure 2:
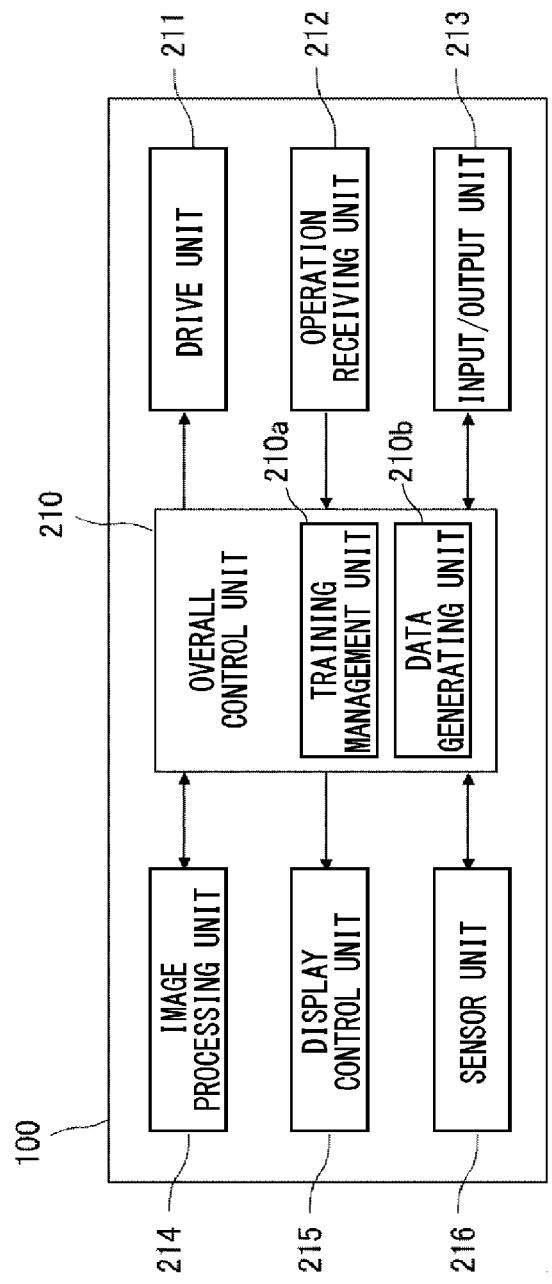
FIG. 2 is a block diagram showing a configuration of a walking training apparatus.

FIG. 2 is a block diagram showing a configuration of the walking training apparatus 100. The overall control unit 210 is, for example, an MPU, and controls the overall operation of the apparatus by executing a control program loaded from the system memory. A drive unit 211 includes a motor and its drive circuit for each of the belt 132, the front pulling unit 135, the rear pulling unit 137, and the walking assistance apparatus 120, which are disposed in a distributed manner. The overall control unit 210 performs drive control by transmitting drive signals to the respective drive units 211. For example, the overall control unit 210 adjusts the rotation speed of the belt 132 according to the set walking speed and turns the motors of the front and rear pulling units 135 and 137 on/off in synchronization with the timing at which the diseased leg is changed from a leg-standing state to a leg-idling state.

An operation receiving unit 212 receives an input operation performed by the trainee 900 or an operator and transmits an operation signal to the overall control unit 210.

The trainee 900 or the operator operates operation buttons provided in the apparatus, a remote controller belonging to the apparatus, or the like, which constitutes the operation receiving unit 212, and thereby provides an instruction to turn on/off a power supply, to start a training, enters numerical values for the setting, or selects a menu item.

An input/output unit 213 includes, for example, a USB interface, and is a communication interface to connect the external communication apparatus 300 or other external apparatuses. The overall control unit 210 communicates with the external apparatus through the input/output unit 213. By doing so, the overall control unit 210 rewrites a training program, receives commands, and outputs generated training data.

An image processing unit 214 generates image data by image-processing an image signal received from the camera 140 according to an instruction received from the overall control unit 210. Further, the image processing unit 214 can perform a specific image analysis by image-processing an image signal received from the camera 140 according to an instruction received from the overall control unit 210. For example, the image processing unit 214 detects a position of the diseased leg (leg-standing position) in contact with the treadmill 131 by performing an image analysis. Further, the image processing unit 214 can generate image data by performing a trimming or the like in order to adapt image data to the data format of training data. For example, the image processing unit 214 cuts out an area near the foot (hereinafter referred to as a foot area) from the image data when generating moving image data of the moving leg.

A display control unit 215 receives a display signal from the overall control unit 210, generates a display image, and displays the generated image on the training monitor 138. The display control unit 215 generates images showing the progress of the training and real-time video images taken by the camera 140 according to the display signal.

A sensor unit 216 includes various sensors disposed in a distributed manner and their drive circuits. The overall control unit 210 performs sensing control by transmitting a sensing starting signal or an output request signal for each of the sensors to the sensor unit 216. The overall control unit 210 processes received sensor outputs, records the processed data on the training data, performs feedback for the subsequent control, and so on.

The overall control unit 210 also functions as a function performing unit which performs various calculations and controls related to the control. A training management unit 210a controls the walking training apparatus 100 according to a training program and successively collects information on the walking training of the trainee 900. A data generating unit 210b generates training data in a predetermined format from the information on the walking training collected by the training management unit 210a, the state of the apparatus, information attributed to the trainee 900 himself/herself, and so on.

Figure 3:
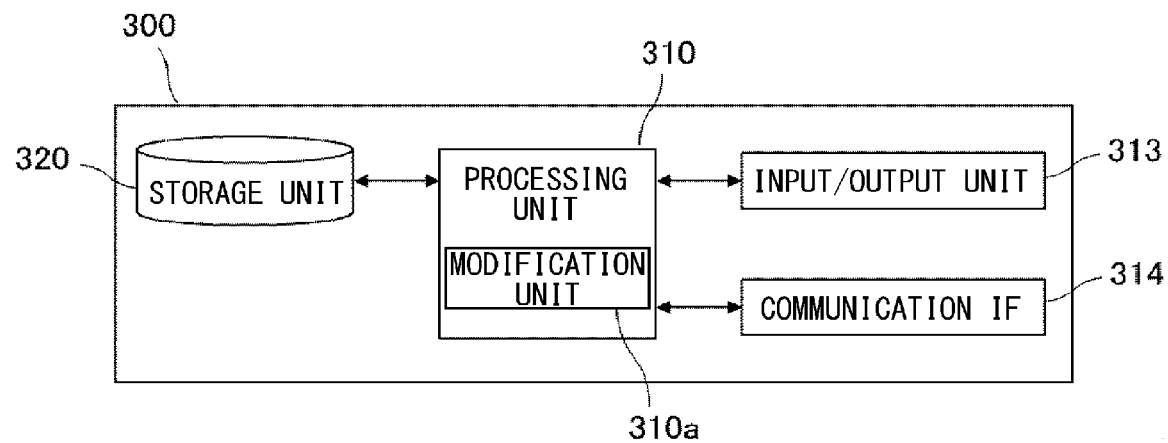
FIG. 3 is a block diagram showing a configuration of an external communication apparatus.

FIG. 3 is a block diagram shows a configuration of the external communication system 300. A processing unit 310 is, for example, an MPU, and performs processes which the external communication apparatus 300 is in charge of by executing a control program loaded from the system memory.

The input/output unit 313 includes, for example, a USB interface, and is a communication interface for connecting for communication with the walking training apparatus 100. The processing unit 310 communicates with the walking training apparatus 100 through the input/output unit 313. Further, the processing unit 310 receives training data output from the walking training apparatus 100 and transmits various request signals to the walking training apparatus 100.

A communication IF 314 includes, for example, a wireless LAN interface, and is a communication interface for connecting the Internet network 400. In the example shown in FIG. 1, the communication IF 314 connects the Internet network 400 by using a wireless communication device 410 as an access point. The processing unit 310 communicates with the server 500 through the communication IF 314. Further, the processing unit 310 receives a modification instruction of training data from the server 500, modifies designated training data according to the modification instruction, and transmits modified data to the server 500.

A storage unit 320 is, for example, a HDD, and stores training data. The processing unit 310 writes training data (hereinafter, in particular, may be referred to as "raw training data") received from the walking training apparatus 100 through the input/output unit 213 into the storage unit 320. Further, the processing unit 310 writes training data (hereinafter, in particular, may be referred to as "modified training data") modified according to a modification instruction into the storage unit 320. When training data requested from the server 500 through the communication IF 314 has already been stored as modified training data in the storage unit 320, the processing unit 310 reads the modified training data from the storage unit 320 and transmits the read modified training data to the server 500.

The processing unit 310 functions as a function performing unit which performs various calculations and controls related to the control. A modification unit 310a, as one of its functions, modifies raw training data into modified training data according to a modification instruction received from the server 500. Note that in this embodiment, raw training data is kept in the storage unit 320 when the modification unit 310a generates modified training data. The processing unit 310 permits an external terminal to view raw training data only when the external terminal is connected through the input/output unit 313. That is, the processing unit 310 permits the external output of raw training data only when the external output is performed through the input/output unit 313, and prohibits the external output of raw training data when the external output is performed through the communication IF 314. With such structures, it is possible to prevent personal information of the trainee 900 from being leaked from an external network and ensure opportunities for specific viewers such as a doctor to examine training data before it is modified.

Figure 4:
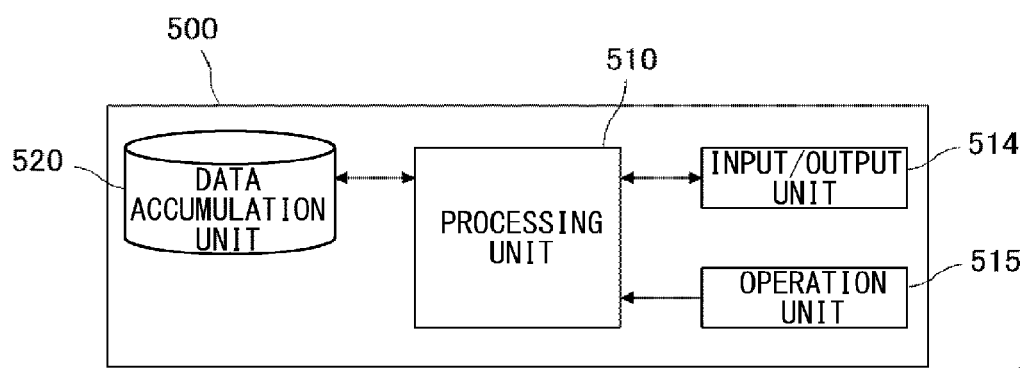
FIG. 4 is a block diagram showing a configuration of a system server.

FIG. 4 is a block diagram showing a configuration of the server 500. A processing unit 510 is, for example, an MPU, and controls the server 500 by executing a control program loaded from a system memory.

A communication IF 514 includes, for example, a wired LAN interface, and is a communication interface for connecting for communication with the Internet network 400. The processing unit 510 transmits a modification instruction of training data to the communication apparatus 300 and receives modified training data from the external communication apparatus 300 through the communication IF 514. Further, the processing unit 510 transmits modified training data to the terminal 600 according to a request from the terminal 600. Further, the processing unit 510 may receive an instruction for specifying an operation performed by the server 500 from the terminal 600.

An operation unit 515 is an input device such as a keyboard or a mouse connected to the main server unit, and is operated by a system administrator when he/she creates a modification instruction, etc. The operation unit 510 receives an operation processing of the operation unit 515. Further, the operation unit 510 generates a modification instruction in conformity with a predetermined command format and requests the external communication apparatus 300 to perform a specific processing.

A data accumulation unit 520 is, for example, an HDD, and stores modified training data. The processing unit 510 writes modified training data received from the external communication apparatus 300 through the communication IF 514 into the data accumulation unit 520. Further, the processing unit 510 reads modified training data requested from the terminal 600 through the communication IF 514 from the data accumulation unit 520 and transmits the read data to the terminal 600.

A walking training apparatus authenticated as a medical device is used according to laws or guidelines regarding medical devices. Thus, in general, once a walking training apparatus is used, its structure and control program are prohibited from being altered. Meanwhile, since such laws or guidelines may be revised and there is an influence of public opinion that changes with time, the range of personal information that needs to be protected changes. In the past, when the protection range of personal information on training data to be output has been changed, it has been necessary for the walking training apparatus to be authenticated again as a medical device after the software is updated.

Contrary to the above, the walking training apparatus 100 according to this embodiment adopts specifications according to which training data are output as it is (i.e., raw training data is output) from the input/output unit 213 without performing a mask process or encryption for protecting personal information. However, since the walking training apparatus 100 does not have a function of directly connecting to an external network as described above, it eliminates the possibility that raw training data in which personal information is not protected may be stolen by a malicious outsider.

Next, raw training data will be described. FIG. 5 shows a state in which an example of raw training data which is training data before it is modified is visibly displayed. The raw training data is formed by associating a main file, where information attributed to the trainee 900 such as a name and the training result of the trainee 900 are compiled, with a related image file.

As shown in FIG. 5, by displaying the raw training data on a viewing monitor, a viewer such as a doctor can visually recognize the attributed information, the training result, the image data and the like of the trainee 900. Examples of attributed information include a trainee ID, a name, a sex, a date of birth, an age, and a face photograph (identification image). These information items identify the trainee 900. An identification image itself may be in a format in which an image data is embedded in the main file or a format in which link information for an image file is written in the main file.

Examples of training results include an average evaluation value of training, vital information such as a pulse change, a comment from a physical therapist who has accompanied the trainee in the training, a moving image of a moving leg, and detailed data of each trial. Regarding the moving image, in the example shown in FIG. 5, a moving image of a foot area obtained by trimming an image taken by the camera 140 and a side moving image taken by a side camera (not shown in FIG. 1) are captured as link information. For the moving image of the foot area, for example, a moving image file named "A000325.mp4" is linked. When images are taken in each of a plurality of trials, a plurality of moving image files are linked. In addition, names of a physical therapist who has accompanied a trainee, an administrator who creates training data or the like are recorded as a part of training data.

In the raw training data described above, for example, a name of the trainee 900 or a face of the trainee 900 in the side moving image may be personal information. It is undesirable that such personal information is stolen by a malicious third party in the distribution process on the Internet network 400. However, which items should be protected as personal information changes according to the influence of public opinions changing with the time or the like as described above. Thus, in the walking training system according to this embodiment, a system administrator determines which items should be protected as personal information. The system administrator inputs the determined item by operating the operation unit 515 of the server 500 and the processing unit 510 generates, for example, an instruction for modifying a file format in response to the administrator's operation.

FIG. 6 shows contents of a modification instruction file. According to the modification instructions shown in FIG. 6, "unmodifiable" is entered in each of a name, a date of birth, and an identification image. That is, it is indicated that they should be deleted from the training data. Further, "classification (according to generation)" is entered for ages. That is, it is indicated that specific ages should be expressed in generations such as 10s or 20s. Further, "face mosaic (or pixelization) processing" is entered for a moving-leg video image. That is, it is indicated that mosaic processing should be performed on a face area included in the image. The processing unit 510 of the server 500 generates such modification instruction and transmits the generated instruction to the external communication apparatus 300 before receiving a request for transmitting training data. The modification unit 310a of the external communication apparatus 300 modifies raw training data stored in the storage unit 320 according to the modification instruction received through the communication IF 314.

Figure 7:
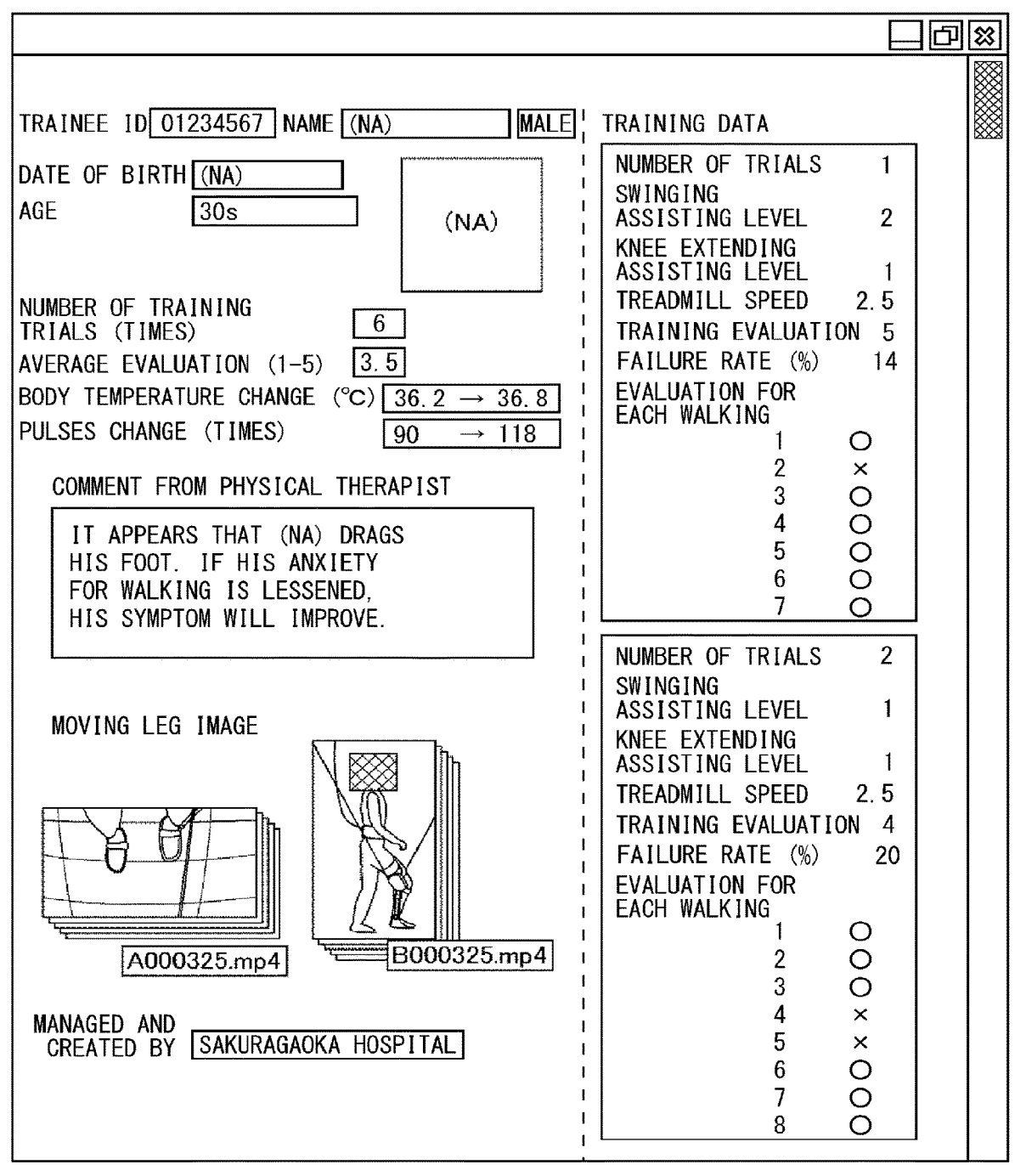

Next, modified training data will be described. FIG. 7 shows a state in which an example of modified training data which is training data after it is modified is visibly displayed. The example shown in FIG. 7 is obtained by modifying the example shown in FIG. 5 according to the modification instruction shown in FIG. 6.

When the modified training data is displayed on the viewing monitor as shown in FIG. 7, (NA) (i.e., no viewing description) is displayed in each of the sections for the name, the date of birth, and the face photograph. Further, although the name of the trainee 900 has been mentioned in the physical therapist comment section in the raw training data, the name is also replaced with (NA). That is, when the modification unit 310a modifies a name according to a modification instruction, the modification unit 310a makes a search as to whether a name is described in other description sections, and thereby modifies the name if it is found. The above-described search is not limited to the name. That is, when other attributed information similar to the name is in other description sections in addition to in the description section for describing the attributed information, the modification unit 310a also modifies the description in the other description sections.

Further, it is shown that the age, which was indicated as "32 years old" in the raw training data, is modified to "30s". Further, it is shown that in the side moving image, which is one of the moving-leg video images and in which the face of the trainee 900 appears, mosaic processing is performed on the face area. Note that the processing performed for images is not limited to mosaic processing and other mask processing such as blurring may be used. As a purpose of concealing personal information for images, more sophisticated processing can be used.

FIG. 8 shows other examples of modifying images. For example, when it is indicated that a "body shape" should be modified in a modification instruction, the body shape of the trainee 900 is modified so as not to be revealed. Regarding the moving-leg video image, since only a gait of a diseased leg needs to be determined, image processing which replaces a side image with a CG (Computer Graphics) can be adopted as a method for concealing a body shape.

Specifically, as shown in FIG. 8, the modification unit 310a generates a CG moving image of a so-called stick person model, in which a body trunk (TL), a thigh (HL), a lower leg (CL), and a leg (FL) relating to a gait of a diseased leg are represented by sticks, and a hip joint (HJ), a knee joint (NJ), and an ankle joint (FJ) are represented by circles. A viewer can confirm the gait of the diseased leg of the trainee 900 even by such the CG moving image.

As described above, raw training data is modified into modified training data according to contents specified by a modification instruction. Therefore, even when modified training data distributed on the Internet network 400 is stolen, personal information of the trainee 900 is not spread. Further, a system administrator can appropriately modify personal information to be protected by regenerating a modification instruction according to the needs of the times etc. For example, when it is desired to newly protect vital information as a subject of personal information, "unmodifiable" may be entered in items (i.e., sections) such as a "body temperature change" section or a "pulse change" section in a modification instruction.

The entity that modifies raw training data according to a modification instruction is the external training apparatus 300. That is, the walking training apparatus 100 only outputs raw training data regardless of regeneration of a modification instruction. Thus, since there is no need to alter the structure or the software of the walking training apparatus 100, the walking training apparatus 100 can be continuously used without being authenticated again as a medical device.

Figure 9:
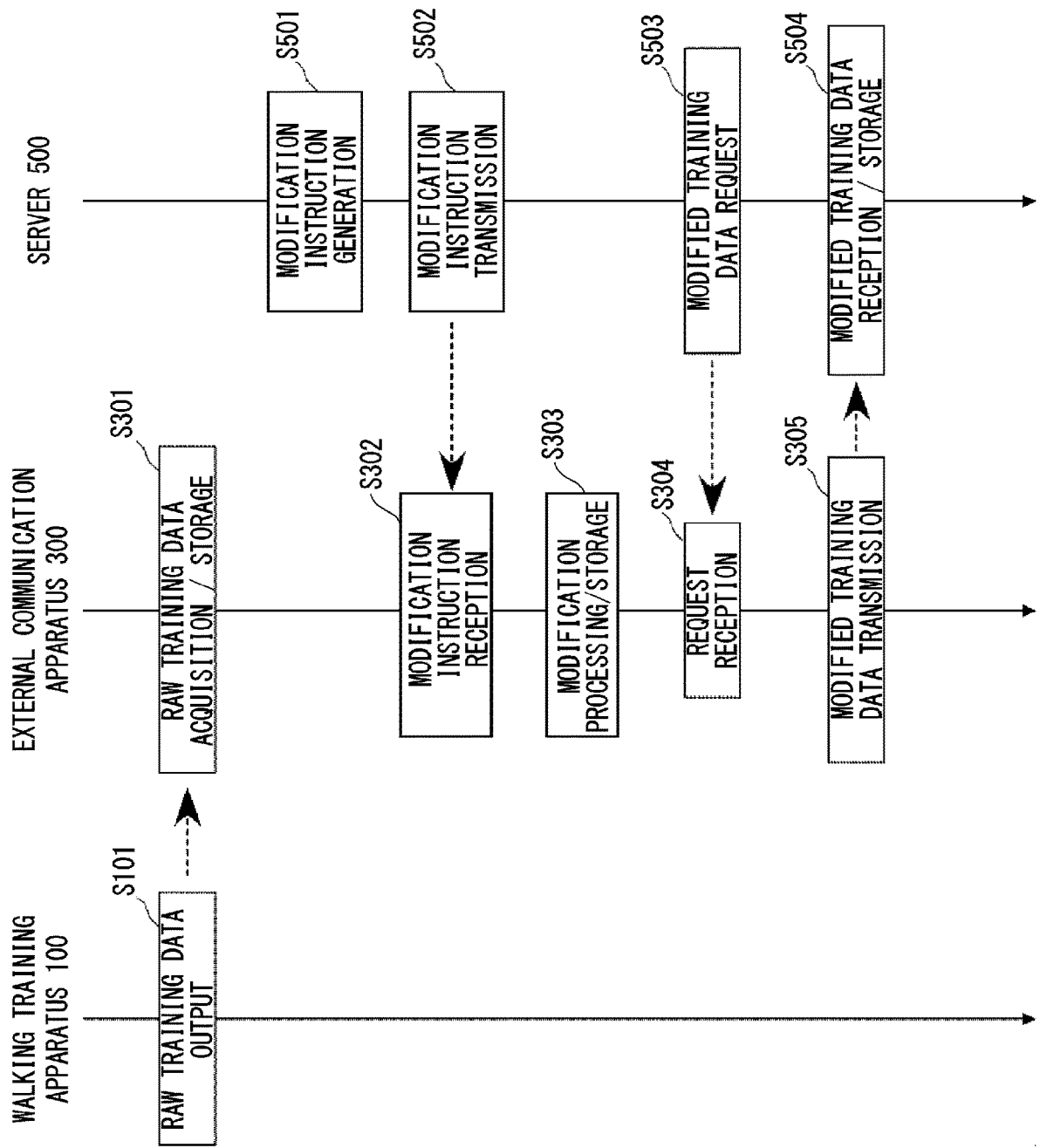
FIG. 9 is a processing flowchart of a walking training apparatus, an external communication apparatus, and a server.

Next, processing flows of data communication programs for controlling each of the walking training apparatus 100, the external communication apparatus 300, and the server 500 will be described. FIG. 9 is a processing flowchart of the walking training apparatus, the external communication apparatus, and the server. The processing flow starts at the point when the trainee 900 has finished the training by using the walking training apparatus 100. Note that the downward arrow on the left indicates a progress of the process performed by the walking training apparatus 100; the downward arrow in the middle indicates a progress of the process performed by the external communication apparatus 300; and the downward arrow on the right indicates a progress of the process performed by the server 500. Further, FIG. 9 shows that processes horizontally connected by an arrow indicated by dotted line are performed roughly at the same time as each other.

In the walking training apparatus 100, when the training management unit 210a finishes a series of training trials, the data generating unit 210b adjusts collected training data, information attributed to the trainee 900 and the like according to a predetermined format and generates raw training data in a step S101. Then, the generated raw training data is output to the external communication apparatus 300 through the input/output unit 213. In a step S301, the processing unit 310 of the external communication apparatus 300 acquires the raw training data output from the walking training apparatus 100 through the input/output unit 313, and stores the acquired data in the storage unit 320.

In a step S501, the processing unit 510 of the server 500 receives an input operation from a system administrator through the operation unit 515 and generates a modification instruction. Then, in a step S502, the generated modification instruction is transmitted to the external communication apparatus 300 through the communication IF 514. The processing unit 310 of the external communication apparatus 300 receives the modification instructions in a step S302. Note that the timing at which the modification instruction is received may be before the raw training data is acquired (step S301).

The modification unit 310a of the external communication apparatus 300 reads the raw training data stored in the step S301. Further, the modification unit 310a modifies the raw training data according to the modification instruction received in the step S302 and generates modified training data (step S303). Then, the external communication apparatus 300 stores the generated modified training data to the storage unit 320.

In a step S503, the processing unit 510 of the server 500 transmits a request for the modified training data to the external communication apparatus 300. The request for the modified training data is generated, for example, at a predetermined time or according to a request from the terminal 600. Upon receiving the request for the modified training data from the server 500 (step S304), the processing unit 310 of the external communication apparatus 300 reads the requested modified training data from the storage unit 320 and transmits the read data to the server 500 through the communication IF 314 in a step S305.

In a step S504, when receiving the requested modified training data, the processing unit 510 of the server 500 stores the modified training data in the data accumulation unit 520. Further, the modified training data received according to the request from the terminal 600 is transmitted to the terminal 600. The above-described processing is performed each time when the walking training apparatus 100 outputs raw training data.

Further, in the flow described above, the transmission of the modification instruction (step S502) and the request for the modified training data (step S503) are shown as separate processes. However, upon receiving the modification instruction (step S302), the external communication apparatus 300 may successively transmit training data starting from the one in which the modification has just been completed (modified training data) to the server without receiving the request for the modified training data. In this case, the modified training data may not be stored in the storage unit 320.

Further, in the case the external communication apparatus 300 receives the modification instruction (step S302) before acquiring the raw training data (step S301), the modification unit 310a may successively modify the acquired raw training data and transmit the modified data to the server 500. Also in this case, the modified training data may not be stored in the storage unit 320.

In this embodiment as described above, the walking training apparatus 100 does not include a function of connecting for communication with an external network, and the external communication apparatus 300 prohibits raw training data stored in the storage unit 320 from being output to an external network. In this case, when an authorized doctor or the like views the raw training data, he/she detaches the external communication apparatus 300 from the walking training apparatus 100 and carries it with him/her. Then, the doctor connects it to his/her own terminal through the input/output unit 213. By physically carrying the external communication apparatus 300 as described above, the doctor or the like can view the raw training data in his/her own terminal. Note that if a dedicated network is constructed, raw training data may be distributed only when it is distributed within the dedicated network. In this case, the dedicated network is different from an external network where a third party may intervene.

In this embodiment as described above, the walking training apparatus 100 as an example of medical devices has been described. The medical device is not limited to those for rehabilitation such as the walking training apparatus 100. That is, in other medical devices which output various medical data, a range of protection of personal information included in medical data can be flexibly changed by interposing a medical data communication apparatus such as the external communication apparatus 300 as a peripheral device. Further, the medical data can be safely distributed to an external network.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g., magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g., electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A medical data communication apparatus comprising:
a processor configured to:
   acquire raw medical data of a subject output from a medical device, the medical device being connected for communication with the medical data communication apparatus via a first communication interface without an external network intervening therebetween, the first communication interface being a physical communication interface, the raw medical data includes a description section in which information attributed to the subject is described, wherein the information attributed to the subject includes at least one of a name, a date of birth, a body shape image, and a face photogra ph;
   modify the raw medical data to generate modified medical data such that the name, the date of birth, and the face photograph are replaced with text that anonymizes the information attributed to the subject by removing personal identifying information of the subject from the information attributed to the subject, and the body shape image is replaced with a computer-generated image that conceals the personal identifying information and identifies only medically-relevant features of the body shape image,
   wherein the raw medical data is modified based on a modification instruction generated by and received from a server, the server being connected for communication with the medical data communication apparatus via a second communication interface that is connected for communication with the external network and is separate from the first communication interface, the second communication interface being a network communication interface, the modification instruction being for modifying specific information in the raw medical data, the specific information being specified in the modification instruction generated by the server;
   output the modified medical data via the second communication interface to the external network based on a request from the server;
   permit external output of the raw medical data only when the external output is requested via the first communication interface; and
   prohibit the external output of the raw medical data when the external output is requested via the second communication interface,
   wherein the server is configured to transmit the modification instruction through the external network before the server receives the modified medical data, and receive the modified medical data through the external network.

2. The medical data communication a pparatus according to claim 1, wherein
the raw medical data includes image information of the subject, and
the processor is configured to perform a mask processing on at least a part of the image information based on the modification instruction togenerate the modified medical data.

3. The medical data communication apparatus according to claim 1, wherein
the raw medical data includes image information of the subject, and
the processor is configured to replace the image information with a computer graphic based on the modification instruction to generate the modified medical data.

4. The medical data communication apparatus according to claim 1, wherein when the attributed information described in the description section is modified based on the modification instruction to generate the modified medical data, the processor is configured to:
make a search as to whether the described attributed information is included in a section other than the description section in the modified medical data, and
modify the attributed information found in the search such that the attributed information found in the search is replaced with text.

5. A medical data communication method comprising:
acquiring raw medical data of a subject output from a medical device, the medical device being connected for communication to a medical data communication apparatus via a first communication interface without an external network intervening therebetween, the first communication interface being a physical communication interface, the raw medical data includes a description section in which information attributed to the subject is described, wherein the information attributed to the subject includes at least one of a name, a date of birth, a body shape image, and a face photograph;

receiving a modification instruction for modifying specific information in the raw medical data from a server connected for communication with the medical data communication apparatus via a second communication interface that is connected for communication with the external network and is separate from the first communication interface, the second communication interface being a network communication interface, the modification instruction being generated by the server, the specific information being specified in the modification instruction generated by the server;

modifying, based on the modification instruction, the specific information in the raw medical data to generate modified medical data such that the name, the date of birth, and the face photograph are replaced with text that anonymizes the information attributed to the subject by removing personal identifying information of the subject from the information attributed to the subject, and the body shape image is replaced with a computer-generated image that conceals the personal identifying information and identifies only medically-relevant features of the body shape image;

outputting the modified medical data via the second communication interface to the external network based on a request from the server;

permitting external output of the raw medica l data only when the external output is requested via the first communication interface; and prohibiting the external output of the raw medical data when the external output is requested via the second communication interface, wherein the server is configured to transmit the modification instruction through the external network before the server receives the modified medical data, and receive the modified medical data through the external network.

6. A non-transitory computer readable medium storing a medical data communication program for causing a computer in a medical data communication apparatusto perform:

acquiring raw medical data of a subject output from a medical device, the medical device being connected for communication with the medical data communication apparatus via a first communication interface without an external network intervening therebetween, the first communication interface being a physical communication interface, the raw medical data includes a description section in which information attributed to the subject is described, wherein the information attributed to the subject includes at least one of a name, a date of birth, a body shape image, and a face photograph;

receiving a modification instruction for modifying specific information in the raw medical data from a server connected for communication with the medical data communication apparatus via a second communication interface that is connected for communication with the external network and is separate from the first communication interface, the second communication interface being a network communication interface, the modification instruction being generated by the server, the specific information being specified in the modification instruction generated by the server;

modifying, based on the modification instruction, the specific information in the raw medical data for generating modified medical data such that the name, the date of birth, and the face photograph are replaced with text that anonymizes the information attributed to the subject by removing personal identifying information of the subject from the information attributed to the subject, and the body shape image is replaced with a computer-generated image that conceals the personal identifying information and identifies only medically-relevant features of the body shape image;

outputting the modified medical data via the second communication interface to the external network based on a request from the server;

permitting external output of the raw medical data only when the external output is requested via the first communication interface; and prohibiting the external output of the raw medical data when the external output is requested via the second communication interface, wherein the server is configured to transmit the modification instruction through the external network before the server receives the modified medical data, and receive the modified medical data through the external network.

7. A system comprising:

a medical data communication apparatus; and a server, wherein the medical data communication apparatus comprises a processor configured to:

acquire raw medical data of a subject output from a medical device, the medical device being connected for communication with the medical data communication apparatus via a first communication interface without an external network intervening therebetween, the first communication interface being a physical communication interface, the raw medical data includes a description section in which information attributed to the subject is described, wherein the information attributed to the subject includes at least one of a name, a date of birth, a body shape image, and a face photograph;

modify the raw medical data to generate modified medical data such that the name, the date of birth, and the face photograph are replaced with text that anonymizes the information attributed to the subject by removing personal identifying information of the subject from the information attributed to the subject, and the body shape image is replaced with a computer-generated image that concealsthe personal identifying information and identifies only medically-relevant features of the body shape image, wherein the raw medical data is modified based on a modification instruction generated by and received from the server, the server being connected for communication with the medical data communication apparatus via a second communication interface that is connected for communication with the external network and is separate from the first communication interface, the second communication interface being a network communication interface, the modification instruction being for modifying specific information in the raw medical data, the specific information being specified in the modification instruction generated by the server;

output the modified medical data via the second communication interface to the external network based on a request from the server;

permit external output of the raw medical data only when the external output is requested via the first communication interface; and prohibit the external output of the raw medical data when the external output is requested via the second communication interface, and the server comprises a processor configured to:

transmit the modification instruction through the external network before the server receives the modified medical data, and receive the modified medical data through the external network.

8. The system according to claim 7 further comprising a terminal connected to the external network, wherein the processor of the server is configured to provide the modified medical data to the terminal based upon a request received from the terminal, and the terminal is configured to display the modified medical data received from the server.

9. The medical data communication apparatus according to claim 1, wherein the processor is further configured to, upon reception of the modification instruction from the server, search for each occurrence of the specific information in the raw medical data.

* * * * *